(12) United States Patent
Raman et al.

(10) Patent No.: US 9,114,158 B2
(45) Date of Patent: Aug. 25, 2015

(54) COMPOUNDS AND METHODS OF USE IN ABLATIVE RADIOTHERAPY

(75) Inventors: Venu Raman, Ellicott City, MD (US); Phuoc Tran, Ellicott City, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 14/003,283

(22) PCT Filed: Mar. 9, 2012

(86) PCT No.: PCT/US2012/028475
§ 371 (c)(1),
(2), (4) Date: Sep. 25, 2013

(87) PCT Pub. No.: WO2012/122471
PCT Pub. Date: Sep. 13, 2012

(65) Prior Publication Data
US 2014/0018606 A1    Jan. 16, 2014

Related U.S. Application Data (60) Provisional application No. 61/450,969, filed on Mar. 9, 2011.

(51) Int. Cl.
| | |
|---|---|
| *A61K 51/00* | (2006.01) |
| *A61M 36/14* | (2006.01) |
| *A61K 41/00* | (2006.01) |
| *A61K 31/551* | (2006.01) |
| *A61B 18/18* | (2006.01) |
| *A61N 5/10* | (2006.01) |
| *A61K 31/5517* | (2006.01) |

(52) U.S. Cl.
CPC ............ *A61K 41/0038* (2013.01); *A61B 18/18* (2013.01); *A61K 31/551* (2013.01); *A61N 5/10* (2013.01); *A61K 31/5517* (2013.01)

(58) Field of Classification Search
USPC .......................................... 424/1.11
See application file for complete search history.

(56) References Cited

U.S. PATENT DOCUMENTS

| | | | |
|---|---|---|---|
| 7,662,783 B2 * | 2/2010 | Brooks et al. ................. | 514/1.1 |
| 8,518,901 B2 * | 8/2013 | Hosmane et al. .............. | 514/43 |
| 2005/0220796 A1 | 10/2005 | Dynan et al. | |
| 2011/0009412 A1 * | 1/2011 | Mitchell et al. ............... | 514/243 |
| 2011/0237651 A1 * | 9/2011 | Collard et al. ................ | 514/44 A |

FOREIGN PATENT DOCUMENTS

WO    2010039187 A2    4/2010

OTHER PUBLICATIONS

Kumar et al. (Org. Lett. 2008, 10, 4681-4684).*
Baumann et al. (J. Clin. Oncol. 2009, 27, 3290-3296).*
Kondaskar, A., et al., "Novel, broad spectrum anti-cancer agents containing the tricyclic 5:7:5-fused diimidazodiazepine ring system", ACS Med Chem Lett, (2010), vol. 2, No. 3, pp. 252-256.
Raman, V., et al., "RNA helicases : the next generation of targets for cancer treatment", 2010 MIPS/Philips Molecular Imaging Seminar, Sep. 13, 2010, URL : http://mips.stanford.edu/events/mi_seminar10.html#September.

* cited by examiner

*Primary Examiner* — Michael G Hartley
*Assistant Examiner* — Melissa Perreira
(74) *Attorney, Agent, or Firm* — Johns Hopkins Technology Transfer (57) ABSTRACT

Provided herein is the compound RK-33, or a salt, solvate, stereoisomer, or derivative thereof, which is shown to be an inhibitor if the DEAD box helicase DDX3, in mammalian cells. RK-33 is also provided herein for use as a radiation dose sensitizer in a subject suffering from a proliferative disease and undergoing radiation therapy. Methods of treatment of proliferative diseases, such as cancer with a combination of RK-33 and radiotherapy methods such as stereotactic ablative radiotherapy (SABR) are also provided.

7 Claims, 11 Drawing Sheets

COMPOUNDS AND METHODS OF USE IN ABLATIVE RADIOTHERAPY

CROSS-REFERENCE TO RELATED APPLICATIONS

This application is a 35 U.S.C. §371 U.S national entry of International Application PCT/US2012/028475, having an internation al filing date of Mar. 9, 2012, which claims the benefit of U.S. Provisional Application No. 61/450,969, filed on Mar. 9, 2011, the content of each of the aforementioned applications is herein incorporated by reference in their entirety.

BACKGROUND OF THE INVENTION

Ionizing radiation is widely used for the treatment of solid tumors. Conventional definitive radiation treatment involves multiple treatments, generally 20-40, with low doses (<2-3 Gy) stretching over weeks. Promising evidence indicates that high dose, >15-20 Gy, radiotherapy given in <5 treatments also known as stereotactic ablative radiotherapy (SABR) provides therapeutic benefit to human tumors. The first modern venture into SABR was with the use of stereotactic radiosurgery (SRS) for small intracranial tumors that was made possible by technology allowing for submillimeter delivery precision and steep dose gradients beyond the tumor target. SABR, which is also known as stereotactic body radiation therapy (SBRT) has developed more recently with newer technologic advances to target tumors outside of the brain and includes tumors of practically every major body site. Early clinical experience with SABR in early stage lung cancer and oligometastatic cancer has demonstrated excellent local control of ~90%. However, the extreme doses used for SABR can be associated with prominent normal tissue toxicity. Thus, because of the technical complexity and increased toxicity with delivery of SABR there has been an ongoing search for tumor selective radiation sensitizers that would enable use of lower dose per fraction. In addition, too little is known regarding the mechanisms by which SABR acts on tumors in vivo to assume that conventional dose radiation sensitizers, such as platinum agents, would also enhance SABR.

There still exists, therefore, a need for improved radiation dose sensitizers which will allow effective SABR therapy and significantly lower radiation dosages.

SUMMARY OF THE INVENTION

In the effort to characterize altered cellular pathways that are essential for the transformed phenotype, a member of a RNA helicase family, DDX3, was identified, which is dysregulated in many cancer types including lung cancers. The present invention provides that that targeted treatment of DDX3, using a small molecule inhibitor: RK-33 (a fused diimidazodiazepine), is effective on all lung cancer cell lines tested including a carboplatin resistant cell line. Most importantly using a CCSP-rtTA/tetO-KrasG12D/tetO-Twist1 (CRT) autochthonous transgenic lung cancer mouse model, the methods of the present invention are able to significantly reduce lung tumor burden when RK-33 was administered in combination with SABR (15 Gy ×1) and only minimally with conventionally fractionated radiation (3 Gy ×10) in vivo. The present invention provides the compound RK-33 and derivatives thereof, as a novel radiosenitization agent to enhance the effectiveness of SABR therapy.

In accordance with an embodiment, the present invention provides the compound RK-33, or a salt, solvate, stereoisomer, or derivative thereof, and a pharmaceutically acceptable carrier, for use as a medicament, preferably for use as a DDX3 inhibitor in a mammalian cell or population of cells, more preferably for use as a radiation dose sensitizer in a subject suffering from a proliferative disease and undergoing radiation therapy.

In accordance with another embodiment, the present invention provides a method of treating cancer in a subject comprising a) administering to the subject an effective amount of the pharmaceutical composition comprising compound RK-33, or a salt, solvate, stereoisomer, or derivative thereof, and a pharmaceutically acceptable carrier, in one or more doses, and b) administering ionizing radiation to the subject in proximity to the location of the cancer in the subject.

BRIEF DESCRIPTION OF THE DRAWINGS

FIG. 1 shows immunoblots depicting DDX3 expression in lung cancer cell lines. 1A) DDX3 expression in Beas2B cells exposed to two different concentrations of cigarette smoke condensate (CSC). 1B) DDX3 expression in non-small cell lung cancer cell lines (H23 and A549). Actin was used as a loading control.

DETAILED DESCRIPTION OF THE INVENTION

In accordance with an embodiment, the present invention provides the compound RK-33 and derivatives thereof, as a novel radiosenitization agent to enhance the effectiveness of SABR therapy. RK-33 is a member of a novel class of fused diimidazodiazepines which are provided in PCT/US2009/005273 and are incorporated herein by reference. The structure of RK-33 is provided below.

RK-33

In yet another embodiment, the present invention provides a novel small molecule, RK-33 that fits into the ATP binding domain of DDX3 and induces cell death in cancer cells. Thus, the present invention further provides a method of decreasing DDX3 functions in lung cancer cells induces cell death even in a carboplatin resistant lung cancer cell line, A549, while having little or no toxicity in animals.

In accordance with an embodiment, the present invention provides the compound RK-33, or a salt, solvate, stereoisomer, or derivative thereof, and a pharmaceutically acceptable carrier, for use as a medicament, preferably for use as a DDX3 inhibitor in a mammalian cell or population of cells, more preferably for use as a radiation dose sensitizer in a subject suffering from a proliferative disease and undergoing radiation therapy.

Accordingly, included within the compounds and derivatives of the present invention are the tautomeric forms of the disclosed compounds, isomeric forms including enantiomers, stereoisomers, and diastereoisomers, and the pharmaceutically-acceptable salts thereof. The term "pharmaceutically acceptable salts" embraces salts commonly used to form alkali metal salts and to form addition salts of free acids or free bases, such as those used to improve water solubility. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

Embodiments of the invention also include a process for preparing pharmaceutical products comprising the compounds. The term "pharmaceutical product" means a composition suitable for pharmaceutical use (pharmaceutical composition), as defined herein. Pharmaceutical compositions formulated for particular applications comprising the compounds of the present invention are also part of this invention, and are to be considered an embodiment thereof.

As used herein, the term "treat," as well as words stemming therefrom, includes preventative as well as disorder remitative treatment. The terms "reduce," "suppress," "prevent," and "inhibit," as well as words stemming therefrom, have their commonly understood meaning of lessening or decreasing. These words do not necessarily imply 100% or complete treatment, reduction, suppression, or inhibition.

With respect to pharmaceutical compositions described herein, the pharmaceutically acceptable carrier can be any of those conventionally used, and is limited only by physicochemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

As used herein, the term "a radiation dose sensitizer" means any agent, which when contacted with a cell, population of cell or tissue, increases the susceptibility of that cell, population of cell or tissue to ionizing radiation.

As used herein, the term "proliferative disease" includes cancer and other diseases such as neoplasias and hyperplasias. Cellular proliferative diseases include, for example, rheumatoid arthritis, inflammatory bowel disease, osteoarthritis, leiomyomas, adenomas, lipomas, hemangiomas, fibromas, vascular occlusion, restenosis, artherosclerosis, a pre-neoplastic lesion, carcinoma in situ, oral hairy leukoplakia, or psoriasis. In accordance with one or more embodiments, the term cancer can include, for example cancers of the lung, liver, pancreas, prostate, breast and central nervous system, including glioblastomas and related tumors. In accordance with another embodiment, the term "cancer" includes cancers in tissues that can tolerate high doses of radiation. A high dose of radiation would include doses greater than 2 Gy.

In an embodiment, the cancers treated by the present invention would also include cancers which are resistant to hypoxia, chemotherapy, such as, for example, tamoxifen or taxol resistant cancers, and cancers already resistant to radiation therapy.

In accordance with another embodiment, the present invention provides a method of treating cancer in a subject comprising a) administering to the subject an effective amount of the pharmaceutical composition comprising compound RK-33, or a salt, solvate, stereoisomer, or derivative thereof, and a pharmaceutically acceptable carrier, in one or more doses, and b) administering ionizing radiation to the subject in proximity to the location of the cancer in the subject.

In an embodiment, the term "administering" means that the compounds of the present invention are introduced into a subject, preferably a subject receiving treatment for a proliferative disease, and the compounds are allowed to come in contact with the one or more disease related cells or population of cells in vivo.

As defined herein, in another embodiment, the term "contacting" means that the one or more compounds of the present invention are introduced into a sample having at least one cancer cell and appropriate enzymes or reagents, in a test tube, flask, tissue culture, chip, array, plate, microplate, capillary, or the like, and incubated at a temperature and time sufficient to permit binding and uptake of the at least one compound to the cancer cell. Methods for contacting the samples with the compounds, and other specific binding components are known to those skilled in the art, and may be selected depending on the type of assay protocol to be run. Incubation methods are also standard and are known to those skilled in the art.

As used herein, the term "treatment," as well as words stemming therefrom, includes diagnostic and preventative as well as disorder remitative treatment, including, but not limited to administering one or more doses of radiotherapy to a subject or a cell or population of cells, including the use of SABR, SRS and SBRT methods. It will be understood that a subject may undergo more than one treatment or cycle of radiotherapy to be effective in reducing tumor volume or initiate cancer/target cell death.

Radiation therapy, radio-immunotherapy or pre-targeted radioimmunotherapy are used for the treatment of diseases of oncological nature. "Radiotherapy", or radiation therapy, means the treatment of cancer and other diseases with ionizing radiation. Ionizing radiation deposits energy that injures or destroys cells in the area being treated (the target tissue) by damaging their genetic material, making it impossible for these cells to continue to grow. Radiotherapy may be used to treat localized solid tumors, such as cancers of the skin, tongue, larynx, brain, breast, lung or uterine cervix. It can also be used to treat leukemia and lymphoma, i.e. cancers of the blood-forming cells and lymphatic system, respectively. One type of radiation therapy commonly used involves photons, e.g. X-rays. Depending on the amount of energy they possess, the rays can be used to destroy cancer cells on the surface of or deeper in the body. The higher the energy of the x-ray beam, the deeper the x-rays can go into the target tissue. Linear accelerators and betatrons are machines that produce x-rays of increasingly greater energy. The use of machines to focus radiation (such as x-rays) on a cancer site is called external beam radiotherapy. Gamma rays are another form of photons used in radiotherapy. Gamma rays are produced spontaneously as certain elements (such as radium, uranium, and cobalt 60) release radiation as they decompose, or decay. Another technique for delivering radiation to cancer cells is to place radioactive implants directly in a tumor or body cavity. This is called internal radiotherapy. Brachytherapy, interstitial irradiation, and intracavitary irradiation are types of internal radiotherapy. In this treatment, the radiation dose is concentrated in a small area, and the patient stays in the hospital for a few days. Internal radiotherapy is frequently used for cancers of the tongue, uterus, and cervix. A further technique is intra-operative irradiation, in which a large dose of external radiation is directed at the tumor and surrounding tissue during surgery. Another approach is particle beam radiation therapy. This type of therapy differs from photon radiotherapy in that it involves the use of fast-moving subatomic particles to treat localized cancers. Some particles (neutrons, pions, and heavy ions) deposit more energy along the path they take through tissue than do x-rays or gamma rays, thus causing more damage to the cells they hit. This type of radiation is often referred to as high linear energy transfer (high LET) radiation. Radio-sensitizers make the tumor cells more likely to be damaged, and radio-protectors protect normal tissues from the effects of radiation.

In an embodiment, the present invention provides a method of treating cancer in a subject comprising a) administering to the subject an effective amount of the pharmaceutical composition comprising RK-33 in one or more doses, and b) administering ionizing radiation to the subject in proximity to the location of the cancer in the subject. In another embodiment, the method can be repeated on the subject for 2 or more cycles.

In a further embodiment, the pharmaceutical composition used in the method can include RK-33 and another therapeutic agent or agents.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The term "chemotherapeutic agent" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids.

In a further embodiment, the compositions and methods of the present invention can be used in combination with one or more additional therapeutically active agents which are known to be capable of treating conditions or diseases discussed above. For example, the compositions of the present invention could be used in combination with one or more known therapeutically active agents, to treat a proliferative disease. Non-limiting examples of other therapeutically active agents that can be readily combined in a pharmaceutical composition with the compositions and methods of the present invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

The term "modulate," as used herein means that the expression of DDX3, or level of RNA molecule or equivalent RNA molecules encoding one or more DDX3 protein or protein subunits, or activity of DDX3 protein or protein subunits is up regulated or down regulated, such that expression, level, or activity is greater than or less than that observed in the absence of the modulator. For example, the term "modulate" can mean "inhibit," but the use of the word "modulate" is not limited to this definition.

Typically, an attending physician will decide the dosage of the composition with which to treat each individual subject, taking into consideration a variety of factors, such as age, body weight, general health, diet, sex, compound to be administered, route of administration, and the severity of the condition being treated. By way of example, and not intending to limit the invention, the dose of the compositions of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In another embodiment, the dose of the compositions of the present invention can be at a concentration from about 1 nM to about 100 mM, preferably from about 10 µM to about 50 mM, more preferably from about 100 µM to about 5 mM.

In accordance with an embodiment, the present invention provides a method for screening anti-cancer agents comprising: administering a candidate agent to the CT and/or CRT transgenic mouse, wherein the presence or absence of an effect upon the cancer phenotype in said mouse is indicative of the anti-cancer activity of the candidate agent.

In accordance with a further embodiment, the present invention provides a method for screening for agents which modulate the expression of DDX3 in a cancer cell or population of cancer cells comprising: administering a candidate agent to the CT and/or CRT transgenic mouse, wherein the presence or absence of an effect upon the expression of DDX3 in the cancer cell or population of cells in said mouse is indicative of the modulating activity of the candidate agent.

EXAMPLES

Generating the CRT mice and drug treatment. As shown in the results, the functional utility of CRT mice was validated. CRT mice are generated from combinations of bi-transgenic mice; e.g., CT X CR. CRT mice were activated shortly after weaning, four-five weeks old, by doxycycline administered in their drinking water (up to 2 mg/ml) in a total volume of 350 ml to simultaneously activate both Twist1 and KrasG12D transgenes. Fresh doxycycline containing water was administered weekly. Ten weeks post transgene induction, the mice were imaged by microCT to determine tumor load. Induction of the transgenes and imaging the tumor load by microCT were continuous (weekly) till the end of the experiment. Following induction and establishment of lung tumors, RK-33 (1 mM equivalent to 40 mg/Kg) was injected intraperitoneally in combination with radiation at schedules described in the table below. The number of animals used in each group was 25.

Experimental model of metastasis and drug treatment. To establish the lung tumor metastasis model, $1\times10^5$ A549-td Tomato cells were injected into the tail vein of SCID mice. Two weeks following injection, the animals were injected i.p. with RK-33 (1 mM) three times a week, followed by SABR and an additional week of RK-33 (1 mM 3×) and imaged both by microCT and optical imaging. The number of animals used in each group was 25 (treated and control).

Tumor induction and drug treatment. Induction of lung tumors in the CRT mice and A549 experimental metastasis model was performed as above. Twenty-five mice per group (control and treated) were used. The drug and radiation doses are as indicated below in the table.

TABLE 1

| Lung cancer model | Experiment 1 | Experiment 2 |
|---|---|---|
| 1. CCSP-rtTA/tetO-$Kras^{G12D}$/Luc-tetO-Twist1 (CRT)<br>2. Tail vein injection of A549-tdTomato | 1) Induction of tumors<br>2) 15 Gray radiation<br>3) Group 1 animals - survival; group 2 animals - molecular markers | 1) Induction of tumors<br>2) RK-33 for 1 week (3x 1 mM)<br>3) 15 Gray radiation<br>4) RK-33 - additional week (3x 1 mM)<br>5) Group 1 animals - survival; group 2 animals - molecular markers. |
| | microCT and optical imaging-once every week following tumor induction | |

Determining tumor load in the preclinical model using noninvasive optical imaging. The differences in the tumor load are initially estimated using optical imaging for the experimental lung metastasis model. The animals were imaged pre-drug injection and every week post injection. All live animal fluorescence optical imaging was done using a Xenogen Spectrum system (Alameda, Calif.) within the Johns Hopkins University Molecular Imaging Center. Imaging parameters were selected and implemented through the instruments Living Image® 3.5 software. Images were collected using 570 nm bandwidth excitation filter coupled with a 640 nm emission filter. Bright field photographs were obtained for each imaging time. The merged bright field photograph and fluorescent images were generated using Adobe Photoshop® software. The reported fluorescence images were the real-time unprocessed images.

MicroCT procedures. Presently a small animal radiation research platform for radiation treatment of animals was developed. The platform employs an isocentric gantry design and is equipped with on-board cone-beam CT (CBCT) to facilitate accurate focal irradiation of targets. Thus, the platform mimics human treatment methods currently used in the clinics. The platform employs a dual-focal spot constant-voltage X-ray source (Seifert, Fairview Village, Pa.) for both imaging and irradiation. It is mounted on a gantry with a source-to-isocenter distance of 35 cm. Manual gantry rotation is limited to 120° from vertical in 15° increments. Robotic translate/rotate stages are used to control the positioning of the animal. Depending on the tissue of interest, X-rays of 50 to 100 kVp from the smaller 0.4-mm focal spot are used for imaging. On-board cone beam CT (CBCT) imaging is achieved by a 2-pi rotation of the horizontal animal between the stationary X-ray source and a 20 cm×20 cm flat-panel detector (Perkin Elmer, Santa Clara, Calif.). The flat panel has 512×512 pixels and is positioned to achieve an image magnification of 1.5, resulting in a pixel dimension of 0.26 mm×0.26 mm at isocenter. For practical reasons, CBCT images are reconstructed at 0.52 mm×0.52 mm×0.52 mm voxel resolution. Animals are anesthetized with 2% isofluorane in a nitrogen/oxygen mixture. Reconstructions of the images are processed and then viewed using commercially available software (XVI Launch, Gulmay Medical Limited).

Radiation treatment for CRT mice. The CT imaging dose is less than 2 cGy for 50 kVp and less than 1 cGy for 100 kVp. The approach of the present invention has enabled achievement of a conformal delivery accuracy of 0.2 mm.

Thoracic image-guided irradiation. The animals are anesthetized with 2% isoflurane in 70% $O_2$/30% $N_2$ delivered via a nose cone and repositioned on the platform stage. For whole thorax treatments a 2.5 cm×1.4 cm collimator was used and the positioning of the field is managed via CBCT and robotic gantry adjustments. The final image verification was performed using double exposure imaging with the treatment collimator merged with an open field. Fifteen Gy radiation calculated at the isocenter was delivered using a single posterior field. Fifteen gray was chosen to simulate SABR dosing, which is an increasingly common modality for early stage lung cancer treatment in patients.

Treatment dosimetry is verified for each collimator and a dose rate of 2.28 Gy/min is achieved with this setup. The flat panel detector allows for verification of lung base coverage in the field during radiation and serves as real-time image guidance. For hemi-thorax treatments, a similar procedure is used with a smaller, 0.5 cm×0.9 cm collimator resulting in a slightly lower dose rate of 2.08 Gy/minute (data not shown).

Endpoints for in vivo experiments. The primary endpoint is survival (Group 1 animals in table above). Animals following treatment are monitored daily by animal care staff and 3×/week by investigators for signs of mortality and morbidity. Survival is analyzed by Kaplan-Meir method. A second endpoint involves tumor response using serial imaging. The tumor burden is quantified from the CBCT data set using the image and volume contouring utility of the Pinnacle3 Radiation Therapy Planning software v.8.1y (Philips Inc., Madison, Wis.) used in the clinic for human patients. Each CBCT data set contains full 3D volumetric data for the tumor burden estimation. A board certified Radiation Oncologist and expert in small animal imaging performed the tumor identification and contouring on the Pinnacle work station. The volumes were calculated and plotted over time with appropriate statistical analysis.

Ex vivo histology and immunohistochemistry. Following the treatment regimens above, lung samples are harvested, fixed, sectioned and stained with hematoxylin/eosin to evaluate the number of lung nodules at the defined time points of 1-2 days, 1-, 2- and 4-weeks following treatment (Group 2 animals in table above). Lung tumor sections are immuostained using gH2AX and 53BP1 antibodies to detect the percentage of double stranded breaks. The parallel sections are then stained for apoptosis using Tunel assays as well as for senescing cells by β-galactosidase staining Normal tissues of the thorax, the esophagus and heart are also removed and examined by H&E to compare radiation regimens for differences in normal tissue damage.

Clonogenic assays. About $1\times10^5$ A549 cells were treated with RK-33 (1-6 µM) and to increasing dose of IR (1-20 Gy). After 24 hours, 500 cells from each combination treatment will be plated into a 6-well plate. Following incubation for 1-3 weeks, colonies were fixed in glutaraldehyde (6.0% v/v), stained with crystal violet (0.5% w/v) and counted using a stereomicroscope. Clusters of >50 cells (i.e., six cell doubling times) were scored as colonies. The amount of radiosensitization by RK-33 was determined using the Chou-Talalay equation to determine the combination index (CI). A CI 0.9-1.1 was indicative of additivity while a CI <0.9 indicated synergism. The survival curves, S, were fit to the linear-quadratic model $S=\exp(-\alpha D-\beta D2)$ to determine classical parameters of radiation sensitivity.

Flow cytometric analysis. Following combination treatment, as indicated in the section of clonogenic assays, the cells were harvested, fixed, and stained either with Magic solution (0.56% NP-40, 3.7% formaldehyde, and 0.01 mg/ml Hoechst 33258 in PBS) or propidium iodide (10 µg/ml). Cell cycle analysis was then performed by laser scanning cytometry on a LSR (BD Biosciences, San Jose, Calif.). Experiments were done in replicates and repeated twice. Data were analyzed using ModFit LT 2.0 software (Verity House Software, Topsham, Me.).

Analysis of molecular events following combination treatment. Following treatment, total proteins were extracted and scored for cleaved poly(ADP-ribose) polymerase (PARP), anti-apoptotic proteins such as IAP-2 and Bc1-xL, as well as pro-apoptotic proteins such as Bax, by immunoblotting. The cells were also immunostained for γH2AX foci and for active Caspase-3 with an apoptosis kit.

Example 1

Figure 1A:
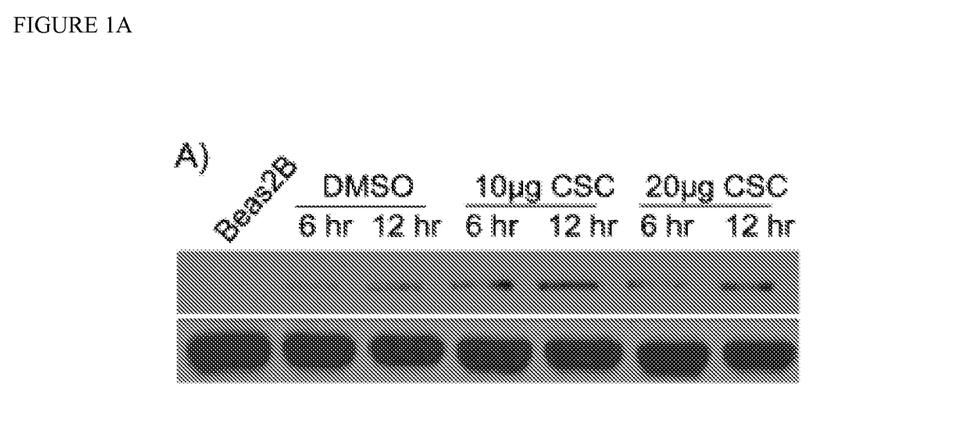
Figure 1B:
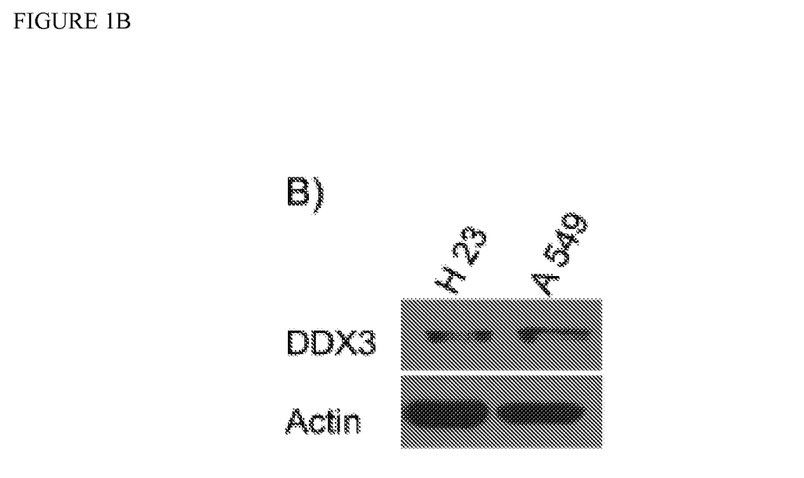
Figure 2:
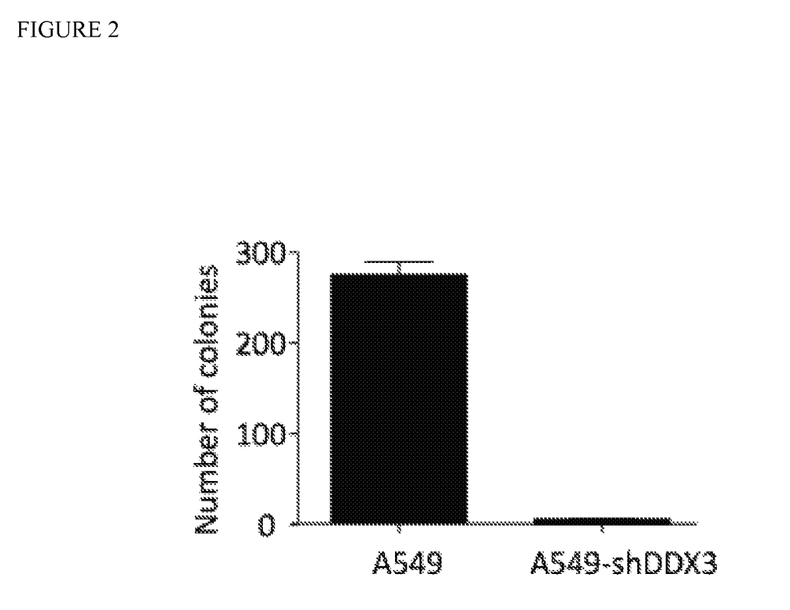
FIG. 2 is a bar graph of the number of colonies formed in soft agar assays using A549 and A549-shDDX3 cells. Experiments were done in triplicate.

The experiments show activation of DDX3 in lung cell lines (FIG. 1A). Moreover, aggressive lung cancer cell lines such as A549 and H23 exhibited robust expression of DDX3 (FIG. 1B). Importantly, down-regulation of DDX3 in A549 abrogated the colony forming abilities in soft agar assays (FIG. 2). Taken together these data indicate that DDX3 is one of the components necessary for lung cancer biogenesis and provides a novel target for lung cancer treatment.

Example 2

Figure 3:
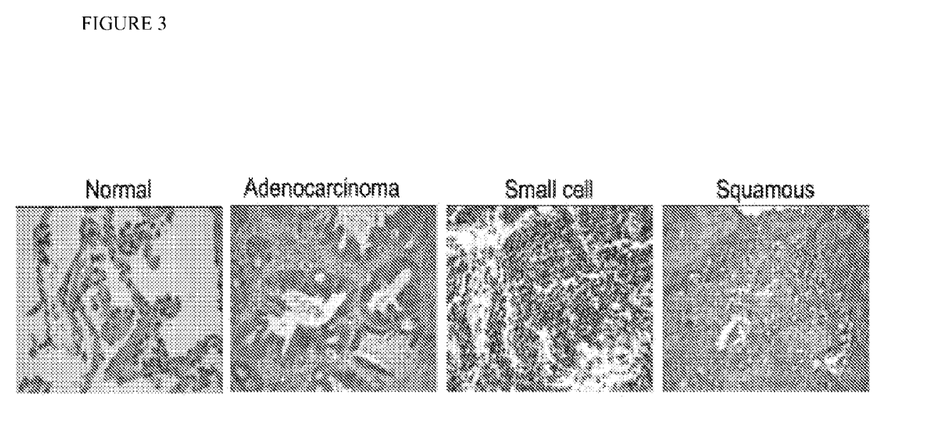
FIG. 3 is a set of photomicrographs depicting expression of DDX3 in normal lung and in different pathological stages of lung cancer. Photomicrographs of the normal lung were taken at 40× magnification and the lung cancer samples at 20×.

DDX3 expression in lung cancer clinical samples. DEAD box helicases have been identified as transcriptional co-activators of both growth promoting and tumor suppressor genes. Thus, we extended our studies to evaluate the expression profile of DDX3 in lung cancer patient samples by immunohistochemistry. As shown in FIG. 3, lung adenocarcinoma sample as well as small cell carcinoma and squamous cell carcinoma showed robust DDX3 expression as compared to the normal lung. Interestingly small cell carcinoma and squamous cell carcinoma had more nuclear staining than the adenocarcinoma sample. This indicates a role for DDX3 in the pathogenesis of human lung cancer.

Example 3

Figure 4:
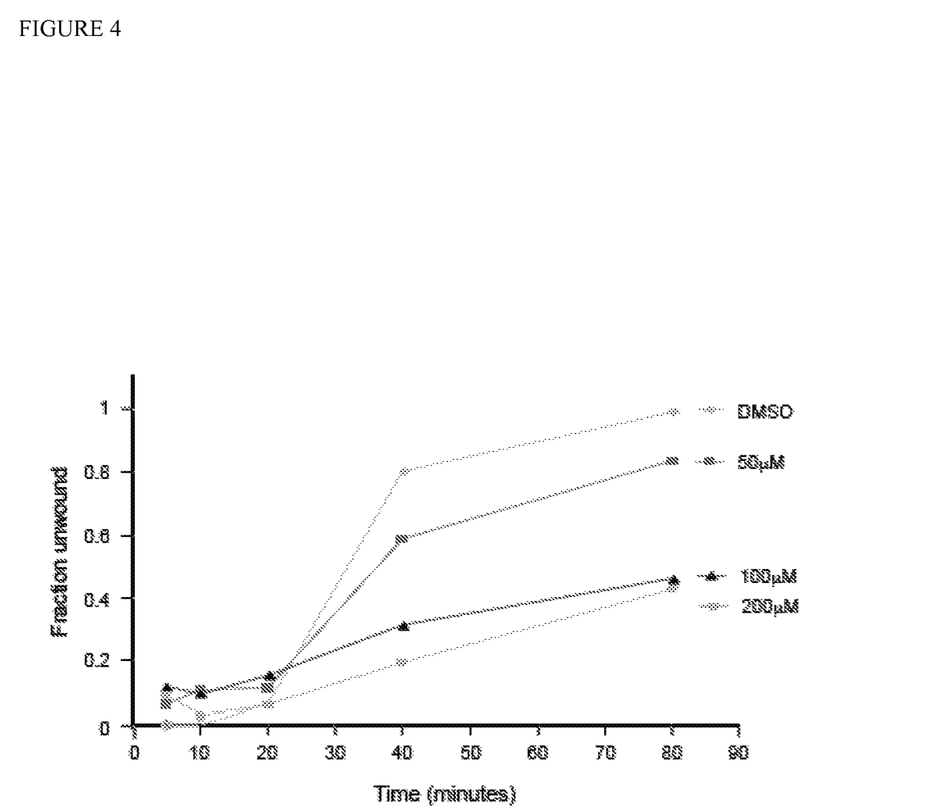
FIG. 4 is a chart showing RK-33 inhibits helicase activity of DDX3.

Generating small molecular inhibitors of DDX3 function. As loss of DDX3 function abrogated colony forming abilities along with increased expression in lung carcinoma samples, a search was initiated to identify molecules that could target a functional substrate binding site of DDX3 protein. Initial work generated a fused diimidazodiazepine ring molecule (RK-33) to target RNA helicase. To confirm the functional activity of RK-33 on DDX3, an in vitro assay was carried out to determine the effects of RK-33 on helicase activity. DDX3 protein was synthesized using the pET system from Novagen. Following DDX3 purification, the unwinding assays were performed using duplex oligos, purified DDX3 and RK-33. Quantification was done by evaluating the pixel density of the native duplex oligos and the unwound oligos. As shown in FIG. 4, 100 μM of RK-33 was able to reduce unwinding of the duplex oligos by at least 60% over a period of 80 minutes. This indicates that RK-33 has the ability to inhibit the unwinding properties of DDX3.

Example 4

Figure 5:
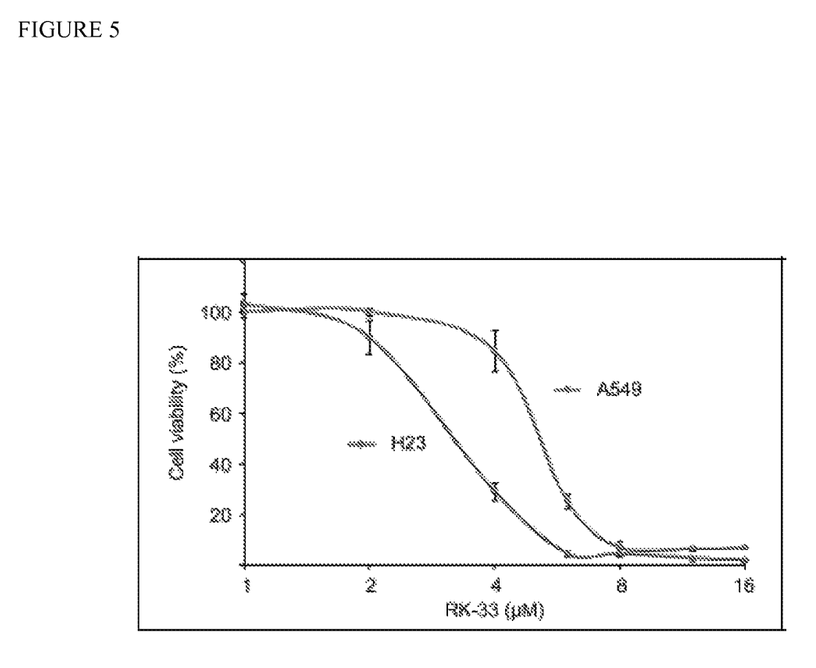
FIG. 5 is a plot showing the effect of RK-33 on two lung cancer cell lines. Lung cancer cell lines were incubated with different concentrations of RK-33. At day 3, MTS assays were performed to determine the percentage of metabolically active cells. The experiments were repeated in triplicate. The $IC_{50}$ values for H23 and A549 are 3.5 and 5 µM respectively.

To study the effects of RK-33 on cell growth and proliferation, lung cancer cell lines (H23 and A549) were used for the initial studies. As shown in FIG. 5, 8 μM of RK-33 was able to efficiently ablate both the cancer cell lines. To the best of our knowledge, this is the first data set of evaluating the efficacy of a small molecule inhibitor of DDX3 to kill lung cancer cells.

Example 5

Figure 6:
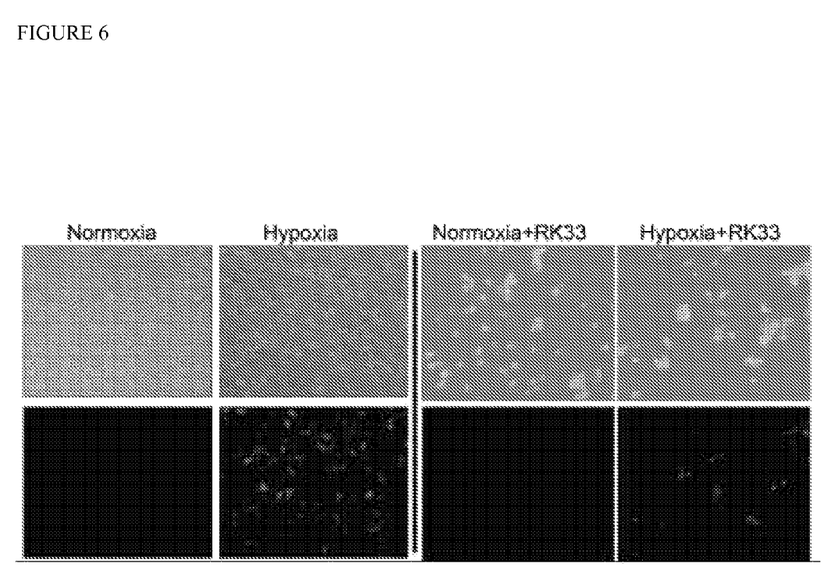
FIG. 6 shows that RK-33 can induce cell death under hypoxic conditions. Cells engineered to express a hypoxia induced red fluorescent protein (tdTomato) were incubated with $CoCl_2$ (hypoxia mimetic compound) for 24 hours, following which RK-33 was added and incubated for 72 hours. Photomicrographs were taken at 20×. Experiments were repeated twice.

Effect of hypoxia on the functional activity of RK-33 to induce cell death. During solid tumor biogenesis, regions of hypoxia develop within the tumor due to inadequate and poorly formed vasculature. These regions have been shown to be resistant to chemo- and radio-therapy and have also been closely linked to malignant progression. In addition, some have posited that tumor hypoxia is a major limiting factor of the curability by SABR at lower radiation dose. Most of the current prescribed chemotherapeutic agents for cancer treatment exhibit inadequacy to induce cell death under hypoxic conditions. To evaluate efficacy of RK-33 to induce cell death under hypoxic conditions, cells were incubated with $CoCl_2$ (hypoxia mimetic compound) for 24 hours, following which RK-33 was added and incubated for 72 hours. As shown in FIG. 6, RK-33 was able to retain its activity both under normoxic and hypoxic conditions, thus making it an excellent agent for cancer treatment in general.

Example 6

Figure 7:
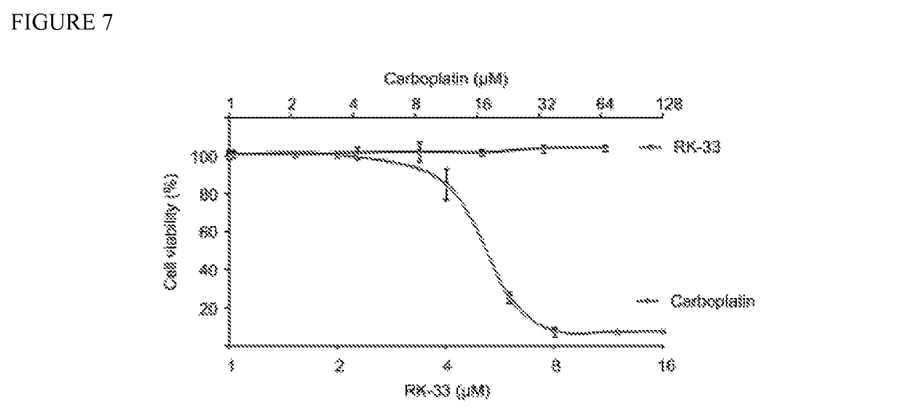
FIG. 7 is a curve depicting a MTS assay demonstrating that A549 cells are resistant to carboplatin but sensitive to RK-33. Experiments were performed in triplicate.
Figure 8:
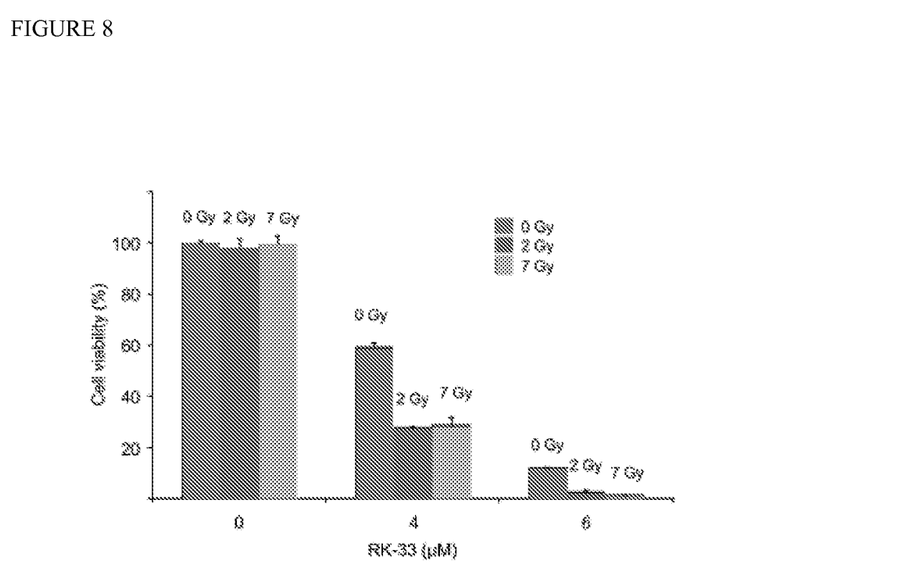
FIG. 8 is a set of bar graphs depicting the effect of radiation and RK-33 on A549 cells. As indicated combination treatment shows synergy with respect to cell killing. Experiments were performed in triplicate.
Figure 12:
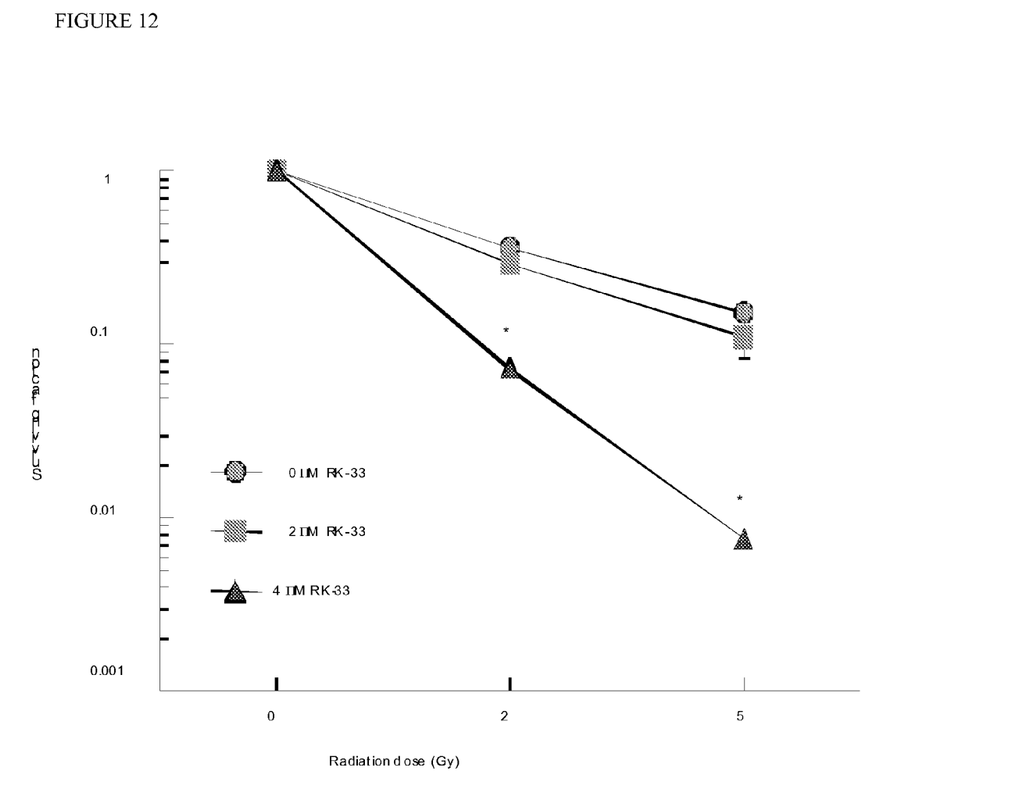
FIG. 12 is a set of survival curves of A549 cells treated with RK-33 and radiation in vitro.

Combinatorial effect of RK-33 and radiation in lung cancer cell line, A549. Given the current treatment protocol for lung cancer patients, which includes chemotherapy and radiation, the cell killing abilities of RK-33 was evaluated in combination with radiation in a chemotherapy/radiation resistant lung cancer cell line, A549 (FIG. 7). As shown in FIG. 8, the combination of RK-33 and radiation was able to kill the cells much more effectively than either treatment alone. For this experiment, RK-33 below the $IC_{50}$ value was used to determine if there was any additive or synergistic effect. A Chou-Talalay based analysis indicated a significant synergistic effect with respect to cell death at 4 and 6 μM concentration of RK-33 with 2 and 7 gray of radiation, as quantified in the bar graph. A survival curve showing A549 cells treated with RK-33 as discussed is showing in FIG. 12.

Example 7

Figure 9:
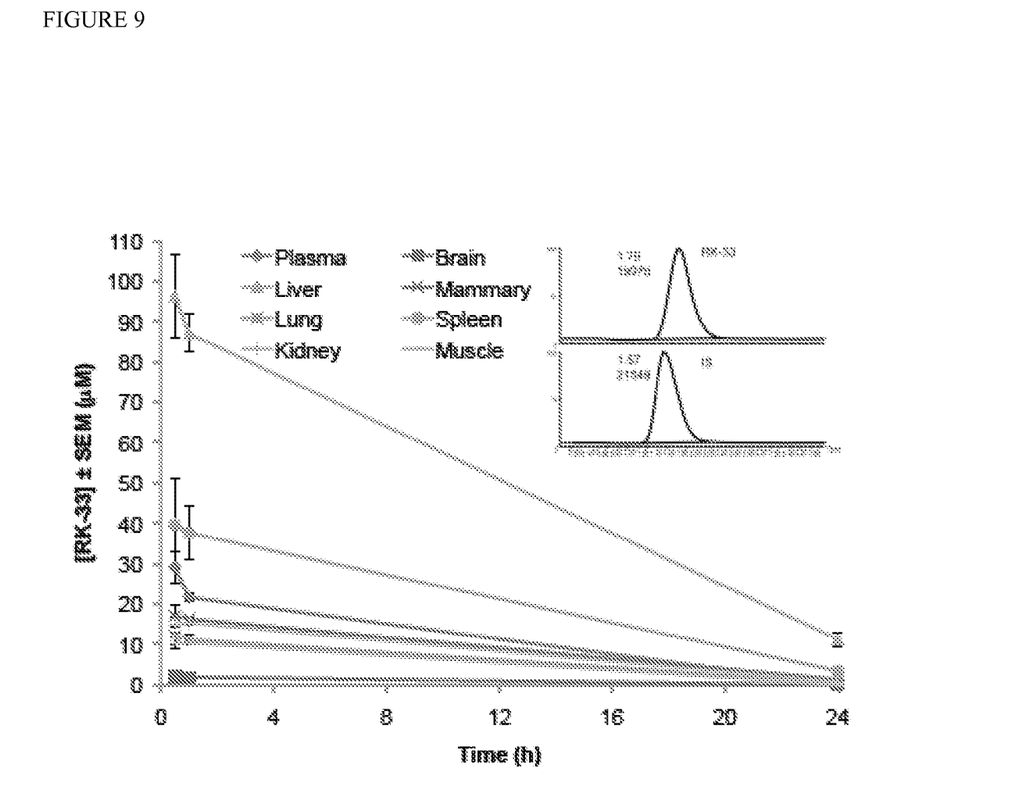
FIG. 9 is a set of curves illustrating the biodistribution of RK-33 in mice at different time intervals using an LC/MS/MS method. A total of five mice per time point were used for this study.

Analysis of the toxicity of RK-33 in SCID mice. An extensive pathological examination of all tissues was performed following necropsy, which indicated no tissue damage. Subsequently, we carried out pharmacokinetics in multiple tissue compartments. For this a LC/MS/MS method was developed for determination of RK-33 in mouse plasma (FIG. 9-inset). Sample preparation involved acetonitrile precipitation and separation of RK-33 and the internal standard, temazepam, was achieved on a Waters Xterra column. As indicated in FIG. 9, brain exposures are well managed and target tissues are well above effective killing concentrations. The animals were injected I.P. (single dose of 20 mg/kg with five animals per arm) and the tissue harvested at different time intervals (30 minutes, 60 minutes and 24 hours) and analyzed.

Example 8

Generation of inducible autochthonous lung tumor mouse models. To test the effect of RK-33 and radiation to treat lung tumors, an autochthonous model was developed by Dr. Tran, which is based on the expression of Twist1 and KrasG12D oncogene expression. Briefly, a tet-inducible Twist1 transgenic mouse model that also co-expresses the luciferase gene was generated. Following validation, the Luc-tetO-Twist1 (T) construct was used for microinjection of single cell embryos, which were implanted into pseudo-pregnant females. Resultant founders screened by polymerase chain reaction (PCR) were bred to the CCSP-rtTA (C) mouse line to produce bitransgenic CT mice. CCSPrtTA mice express rtTA predominantly in alveolar type II pneumocytes and confer lung tissue specificity. It was found that generating a tri-transgenic mouse with KrasG12D oncogene expression [CCSPrtTA/tetO-KrasG12D/Luc-tetO-Twist1 (CRT)] accelerated lung tumor formation as compared to CCSP-rtTA/tetO-KrasG12D (CR) mice. Upon doxycycline treatment, CR mice developed lung tumors with a median latency of 32 weeks.

Figure 10:
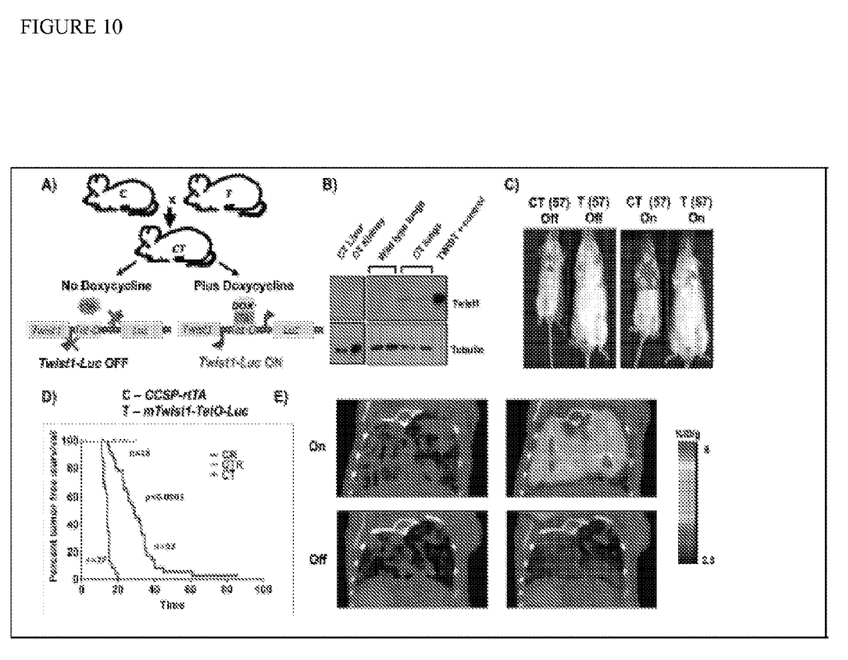
FIG. 10 is a schematic and a series of photographs depicting the generation of an inducible lung epithelial specific Twist1-Luciferase mouse model of the present invention. 10A) Mice containing CCSP-rtTA are crossed with the Twist1-tetO-Luc line and bitransgenic animals (CT) fed doxycycline induce Twist1 and Luc transcription. 10B) The CT transgenic mouse line expresses Twist1 and Luciferase inducible in only the lungs of bitransgenic mice as shown by Western blotting and (10C) BLI on a Xenogen Spectrum. 10D) Twist1 accelerates KrasG12D-induced lung tumorigen- esis from 29 weeks (CR) to 14 weeks (CTR). 10E) CRT tumors regress rapidly following doxycycline withdrawal or turning Off Kras & Twist1 oncogenes by microCT (left panels) and microPET (right panels).

Surprisingly, CRT mice developed lung tumors with a shortened latency period of 15 weeks, indicating Twist1 dramatically accelerates K-rasG12D-induced lung tumorigenesis (log-rank analysis of Kaplan-Meier tumor free survival, $p<0.0001$). These CRT tumors are composed histologically of adenomas/adenocarcinomas, but in contrast to CR lung tumors CRT mice had a greatly increased proportion of adenocarcinomas (FIG. 10).

As both CR and CRT mouse models utilize tetracycline-inducible gene expression systems this model can simulate an oncogene(s) targeted therapy by turning the oncogene(s) "Off" following tumor development. Thus, in an embodiment, the present invention provides a novel transgenic mouse model system of spontaneous autochthonous lung tumors. The CRT transgenic model provides a unique model to test novel preclinical compounds with radiation for the treatment of cancer on autochthonous primary lung tumors in the setting of an immunocompetent host with the complex effects of the tumor microenvironment intact. More importantly, these Twist1 expressing lung tumors also have elevated levels of DDX3 (data not shown).

Example 9

Figure 11:
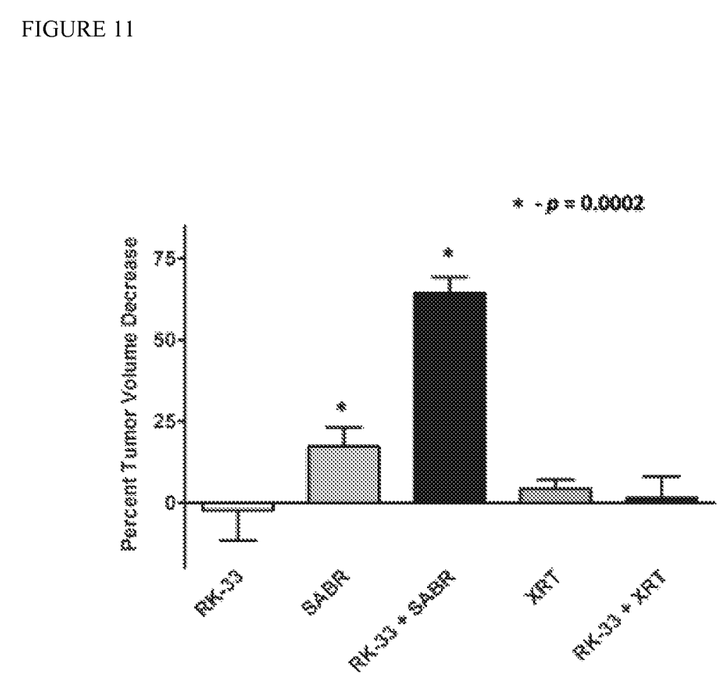
FIG. 11 is a bar graph showing the chemosensitization of RK-33 with radiation to reduce lung tumors in CRT mice. Following RK-33 and radiation treatment, the animals were imaged using microCT (data not shown). The bar graph depicts the reduction of lung tumor volume in n=8 animals per group. The tumor volumes were quantified from the CBCT data set using the image and volume contouring utility of the Pinnacle3 Radiation Therapy Planning software v.8.1y (Philips Inc., Madison, Wis.) used in the clinic for human patients. Each CBCT data set contains full 3D volumetric data for the tumor burden estimation.

Combination treatment of RK-33 and SABR synergizes for clinical response in CRT mice. Following the encouraging results obtained in vitro using RK-33 and radiation, the efficacy of the combination treatment in CRT mice was evaluated. A small pilot of lung tumor moribund CRT animals (n=2-7 per treatment group) were given 3 times a week i.p. injections of RK-33 (1 mM final concentration) or vehicle control for 1 week prior to 15 Gy image guided whole thorax SABR on the SARRP (BED assuming $\alpha/\beta$ of 10 is 37.5 Gy). Animals were then given an additional week of RK-33. Treatment responses were monitored serially by microCT weekly for two weeks. Mice were then sacrificed to carry out histopathology of the lung samples. Whereas each single agent demonstrated stasis or perhaps slight regression, dramatic in vivo synergy was found between RK-33 and SABR as demonstrated by dramatic tumor regression as seen by microCT and ultimately H&E histology of the sacrificed animals (FIG. 11). Similar trends persisted as far out as 4 weeks following treatment.

RK-33 was next tested with standard conventional fractionated radiation. To compare bioequivalent doses, 3 Gy in 10 fractions (BED assuming α/β of 10 is 39 Gy) was chosen. Interestingly, conventional radiation dose (3 Gy ×10) within the experimental setting showed no synergy with RK-33 for reduction in the tumor volume (FIG. 11). Given this finding, it was found that RK-33 has a greater efficacy to reduce lung tumor load with SABR than standard conventional fractionated radiation.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating cancer in a subject comprising:
   a) administering to the subject an effective amount of a radiosensitizing agent comprising RK-33, or a salt, solvate, or stereoisomer thereof, and a pharmaceutically acceptable carrier, in one or more doses for a period of time before an administration of focused ionizing radiation to the subject, wherein the focused radiation is sterotactic ablative radiotherapy (SABR), sterotactic body radiation therapy (SBRT) or sterotactic radiosurgery (SRS); and
   b) administering focused ionizing radiation at a dosage in the range of about 0.1 Gy to about 30 Gy to the subject in proximity to the location of the cancer in the subject.

2. The method of claim 1, further comprising repeating steps a) and b) for 2 or more cycles.

3. The method of claim 1, wherein the period of time in a) before administration of the focused ionizing radiation to the subject is about 5 to 7 days.

4. The method of claim 3, wherein the dose of radiation of b) is 15 Gy.

5. The method of claim 1, wherein the radiosensitizing agent is administered in one or more doses over a period of about a week.

6. The method of claim 1, wherein the method further comprises administration of another chemotherapeutic agent at step a).

7. The method of claim , wherein the method further comprises administration of another chemotherapeutic agent after step b).

* * * * *